United States Patent
Klomp et al.

(10) Patent No.: US 10,031,084 B2
(45) Date of Patent: Jul. 24, 2018

(54) LASER INDUCED BREAKDOWN SPECTROMETRY DETECTOR

(71) Applicant: Nederlandse Organisatie voor toegepast-natuurwetenschappelijk onderzoek TNO, 's-Gravenhage (NL)

(72) Inventors: Dolf Jaap Klomp, 's-Gravenhage (NL); Fokko Pieter Wieringa, 's-Gravenhage (NL); Andrew Statham, 's-Gravenhage (NL)

(73) Assignee: Nederlandse Organisatie voor toegepast-natuurwetenschappelijk onderzoek TNO, 's-Gravenhage (NL)

( * ) Notice: Subject to any disclaimer, the term of this patent is extended or adjusted under 35 U.S.C. 154(b) by 0 days.

(21) Appl. No.: 15/325,252

(22) PCT Filed: Jul. 10, 2015

(86) PCT No.: PCT/NL2015/050509
§ 371 (c)(1),
(2) Date: Jan. 10, 2017

(87) PCT Pub. No.: WO2016/007012
PCT Pub. Date: Jan. 14, 2016

(65) Prior Publication Data
US 2017/0167983 A1   Jun. 15, 2017

(30) Foreign Application Priority Data

Jul. 10, 2014   (EP) ..................... 14176612

(51) Int. Cl.
*G01N 21/25* (2006.01)
*G01N 21/71* (2006.01)
(Continued)

(52) U.S. Cl.
CPC ....... *G01N 21/718* (2013.01); *A61B 5/14546* (2013.01); *A61B 5/14557* (2013.01);
(Continued)

(58) Field of Classification Search
CPC ...... G01N 21/718; G01N 21/05; G01N 21/85; G01N 33/4875; G01J 3/443
See application file for complete search history.

(56) References Cited

U.S. PATENT DOCUMENTS

2010/0172120 A1* 7/2010 Wegh .................. F21S 10/02
  362/84
2010/0225898 A1  9/2010 Lenke et al.
2011/0111968 A1* 5/2011 Okura .................. B01L 7/00
  506/7

OTHER PUBLICATIONS

International Search Report and Written Opinion dated Sep. 29, 2015 for application PCT/NL2015/050509, filed on Jul. 10, 2015, and published as WO/2016/007012 on Jan. 14, 2016 (Applicant—Nederlandse Organisatie voor toegepastnatuurwetenschappelijk onderzoek TNO // Inventor—Klomp, et al.) (11 pages).
(Continued)

*Primary Examiner* — Shawn Decenzo
*Assistant Examiner* — Maurice Smith
(74) *Attorney, Agent, or Firm* — Ballard Spahr LLP

(57) ABSTRACT

A spectroscopy device is disclosed for inline monitoring of analytes in bulk fluid streams, capable of maintaining sterile conditions. The device comprises a cassette suitable for holding a fluid analyte (151) and having a laser entry wall part and a detector wall part, the laser entry wall part arranged to be optically transparent to laser radiation of a predetermined wavelength and the detector wall part arranged to be optically transparent for spectral parts of interest. Laser transmission optics are provided to focus a laser beam to produce a breakdown plasma discharge within the fluid inside the cassette. A photodetector substrate is (Continued)

provided comprising an array of photosensors, tuned to detect characteristic emission lines from the plasma. The photodetector substrate is conformal to at least the detector wall part of the cassette. A placement provision is arranged for user removable placement of the cassette. Dichroic hot and cold mirrors are applied to selectively transmit/reflect excitation laser light and light emitted by the plasma.

15 Claims, 5 Drawing Sheets

(51) Int. Cl.
| | | |
|---|---|---|
| *G01N 21/05* | (2006.01) | |
| *G01N 21/85* | (2006.01) | |
| *G01N 33/487* | (2006.01) | |
| *A61B 5/1455* | (2006.01) | |
| *A61B 5/145* | (2006.01) | |
| *A61M 1/16* | (2006.01) | |
| *A61M 1/36* | (2006.01) | |

(52) U.S. Cl.
CPC ........ *A61M 1/1605* (2014.02); *A61M 1/3609* (2014.02); *G01N 21/05* (2013.01); *G01N 21/85* (2013.01); *G01N 33/4875* (2013.01); *A61M 2205/3306* (2013.01); *G01N 2201/0686* (2013.01)

(56) References Cited

OTHER PUBLICATIONS

Cremers, et al., "Spectrochemical Analysis of Liquids Using the Laser Spark" Applied Spectroscopy, vol. 38. No. 5, 1 Sep. 1984 pp. 721-729.

Knopp, et al., "Laser induced breakdown spectroscopy (LIBS) as an analytical tool for the detection of metal ions in aqueous solutions," Fresenius J Anal Chem, vol. 355. Jan. 1, 1996, pp. 16-20.

Rehse, et al., "Laser-induced breakdown spectroscopy (LIBS): an overview of recent progress and future potential for biomedical applications," Journal of Medical Engineering & Technology. Informa Healthcare. GB, vol. 36. No. 2, 1 Feb. 2012 pp. 77-89.

* cited by examiner

LASER INDUCED BREAKDOWN SPECTROMETRY DETECTOR

CROSS REFERENCE TO RELATED APPLICATIONS

This application is a national phase filing of International Patent Application No. PCT/NL2015/050509, filed Jul. 10, 2015, which claims priority to European Application No. 14176612.1 filed Jul. 10, 2014, both of which are herein incorporated by reference in their entireties.

FIELD

The present invention relates to a detector device for use of laser induced breakdown spectroscopy analysis in fluid media.

BACKGROUND

In fluid media environments, in particular, in analysis of fluids originating from the human body or of fluids destined for insertion into the human body, such as dialysate, haemodiafiltration fluid or blood serum, but also in plant process environments, in the production of desalinated water etc, a desire exists to monitor the fluids' chemical composition or concentrations, in particular of electrolytes and other chemical traces. Common solution for this are in-line conductivity measurement or off-line analytical testing of fluid samples. With a recent progress of laser technology, compact pulsed lasers are becoming available that combine high beam quality with high pulse energy. When carefully focused, such lasers can deliver energy densities that are strong enough to induce optical breakdown in liquids (in the order of $10 \times e10$ W/cm$^2$).

In fluid media it is possible to generate a short lived plasma wherein the emission spectrum is indicative for the plasma composition.

Spectroscopy techniques of these kinds have been demonstrated in "Laser-induced breakdown spectroscopy (LIBS): "An overview of recent progress and future potential for biomedical applications", Rehse et al, Journal of Medical Engineering & Technology, 2012: 36 (20; 77-89). However, many of the applications known to date require complex large and costly arrangements for laser focusing and sensing, in particular since photospectrometers (due to their limited etendue) can only detect a very low portion of the total radiation emitted by the plasma. LIBS systems are generally complex, but this holds even more for fluid systems, where the media itself may hinder effective propagation of emission radiation.

Furthermore, a problem in the art of LIBS is the high energy photon flux that passes through the laser entrance window. A desire exists to provide for an effective and simple constitution to effectively measure the chemical concentration of substances of interest in a fluid medium whilst avoiding optically induced damage to the laser entry wall. For this the inventors sought a solution.

SUMMARY

In an aspect of the invention there is provided the features listed in claims 1 and 15. In particular, a method and spectroscopy device are provided for contactless inherently sterile inline monitoring of fluid analytes. The device comprises a cassette with a fluidic system suitable for inline holding/processing a fluid analyte which has a laser entry wall part and a detector wall part. The laser entry wall part is arranged to be optically transparent to laser radiation of a predetermined wavelength and the detector wall part is arranged to be optically transparent for spectral parts of interest emitted by the laser induced plasma inside the fluid. Laser transmission optics are provided for transmitting a laser beam of the predetermined wavelength from a laser system, via the laser transmission optics to the cassette. The laser transmission optics are arranged for focus the laser beam through the laser entry wall in an excitation spot within the cassette in order to create emission radiation in the fluid analyte. The excitation spot has a point source that allows precise positioning. The detector wall part is arranged so that the excitation spot within the cassette projects emission radiation centrally relative to it. A photodetector substrate is provided comprising an array of photosensors. The photodetector substrate is conformal to at least the detector wall part of the cassette. Each sensor in the array is arranged with a bandpass filter for detection of emission radiation of the plasma in a specific spectral part of interest. In addition, a placement provision is arranged for removable placement of the cassette with its laser entry wall part facing the laser transmission part. Further, a control mechanism is arranged to impinge the laser beam on the excitation spot within the fluid analyte, in order to create the emission radiation; and detect the emission radiation of the plasma via the detector wall part by the array of photosensors in the spectral parts of interest.

BRIEF DESCRIPTION OF THE DRAWINGS

Embodiments of the invention will now be described, by way of example only, with reference to the accompanying schematic drawings in which corresponding reference symbols indicate corresponding parts, and in which.

DETAILED DESCRIPTION

Figure 1A:
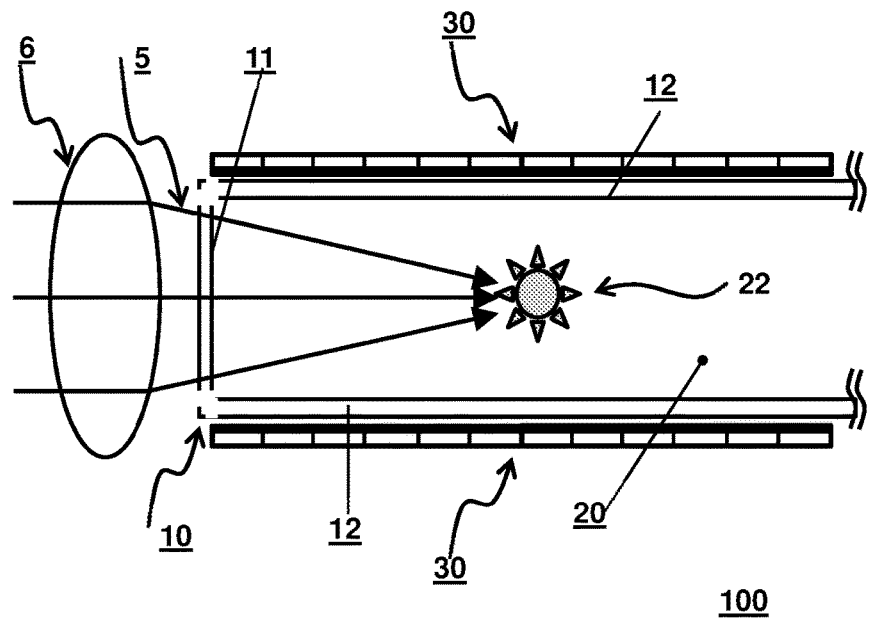
FIG. 1A depicts a spectroscopy device according to an embodiment of the invention.

Unless otherwise defined, all terms (including technical and scientific terms) used herein have the same meaning as commonly understood by one of ordinary skill in the art to which this disclosure belongs as read in the context of the description and drawings. It will be further understood that terms, such as those defined in commonly used dictionaries, should be interpreted as having a meaning that is consistent with their meaning in the context of the relevant art and will not be interpreted in an idealized or overly formal sense unless expressly so defined herein. In some instances, detailed descriptions of well-known devices and methods may be omitted so as not to obscure the description of the present systems and methods. Terminology used for describing particular embodiments is not intended to be limiting of the invention. As used herein, the singular forms "a", "an" and "the" are intended to include the plural forms as well, unless the context clearly indicates otherwise. The term "and/or" includes any and all combinations of one or more of the associated listed items. It will be further understood that the terms "comprises" and/or "comprising" specify the presence of stated features but do not preclude the presence or addition of one or more other features. All publications, patent applications, patents, and other references mentioned herein are incorporated by reference in their entirety. In case of conflict, the present specification, including definitions, will control.

The term "laser entry wall" is used to denote a wall part in the cassette that in use transmits electromagnetic laser radiation of a laser source, so that the laser beam enters the cassette interior. For a typical application for laser radiation systems, such photons may have wavelengths in the NIR or IR area, in particular, wavelengths larger than 800 nm. However, also wavelengths in the visible area of the electromagnetic spectrum may be used, provided an excitation spot within the cassette is provided with sufficient optical energy density in order to create emission radiation in the fluid analyte. With terms "radiation" and "beam" or "light" as used herein encompass all types of high energy electromagnetic radiation, including ultraviolet (UV) radiation, visible light (VIS) and infrared (IR) radiation. The laser entry wall may be physically distinct from other cassette wall parts, for example by suitable optimization of the optical transparency. It may also be integral to the cassette, for example manufactured by moulding.

To avoid damage to the laser entry wall it is important that the wall is highly transparent for the laser wavelength. The laser excitation wavelength does not need to be in the same spectral range as the light emitted by the laser induced plasma. The embodiment in FIG. 3 exploits this.

The term "detector wall part" is used to denote a wall part in the cassette that in use transmits at least spectral parts of interest generated by the laser excited plasma, located within the fluid analyte inside the cassette. The detector wall part is preferably provided integrally to the cassette, but may comprise locally applied coatings and optics in order to enhance its function.

The "array of photosensors" is typically formed on a substrate, e.g. foil or silicon, that is provided with a pixelated array of photo sensitive devices (ccd,cmos,photodiodes), individually or groupwise (in clusters) geared, e.g. by suitable circuitry, to sensing of specific parts of the electromagnetic spectrum. It may be bottom receiving (e.g. ccds provided on a transparent substrate), or top receiving (may comprise one or more processors configured to perform operational acts in accordance with the present systems and methods, such as to provide control signals to the various other components. The "control mechanism" may be a dedicated processor for performing in accordance with the present system or may be a general-purpose processor wherein only one of many functions operates for performing in accordance with the present system. The processor may operate utilizing a program portion, multiple program segments, or may be a hardware device utilizing a dedicated or multi-purpose integrated circuit. Any type of processor may be used such as dedicated or shared one. The processor may include micro-controllers, central processing units (CPUs), digital signal processors (DSPs), ASICs, or any other processor(s) or controller(s) such as digital optical devices, or analog electrical circuits that perform the same functions, and employ electronic techniques and architecture. The controller or processor may further comprise a memory that may be part of or operationally coupled to the controller. The memory may be any suitable type of memory where data is stored. Any medium known or developed that can store and/or transmit information suitable for use with the present systems and methods may be used as a memory. The memory may also store user preferences and/or application data accessible by the controller for configuring it to perform operational acts in accordance with the present systems and methods.

In the disclosure, unless otherwise disclosed with 'placement provision' it is meant that the cassette can be placed by a user, without complicated assembly, in a holder device, for example by sliding action (no form closure), or by locking (form closure) the cassette in the placement provision. The placement provision has geometry that is geared to receiving the cassette. A cassette has its ordinary meaning and can be regarded as equivalent to a holder or a container. The cassette may have provisions for placement and interlocking, as long as they are removably connectable.

In FIG. 1 a first embodiment of the invention is shown, showing a spectroscopy device system 100. The device comprises a cassette 10 suitable for holding a fluid analyte (20) and has a laser entry wall part 11 and detector wall parts 12. The laser entry wall part 11 is arranged to be optically transparent to laser radiation 5 of predetermined a wavelength and the detector wall parts 12 are arranged to be optically transparent for spectral parts of interest to be clarified below. A laser transmission optic 6 is provided for transmitting a laser beam 5 of the predetermined wavelength from a laser system 230 by a control mechanism 220 (See FIG. 6B), via the laser transmission optic 6 to the cassette 10. The laser transmission optic 6 is arranged to focusing the laser beam 5 through the laser entry wall in an excitation spot 22 within the cassette in order to create a breakdown plasma, which emits optical radiation from within the fluid analyte 20. The excitation spot is a small volumetric part of the fluid analyte where the momentary laser power density is sufficiently high to create a short-living breakdown plasma discharge.

Figure 1B:
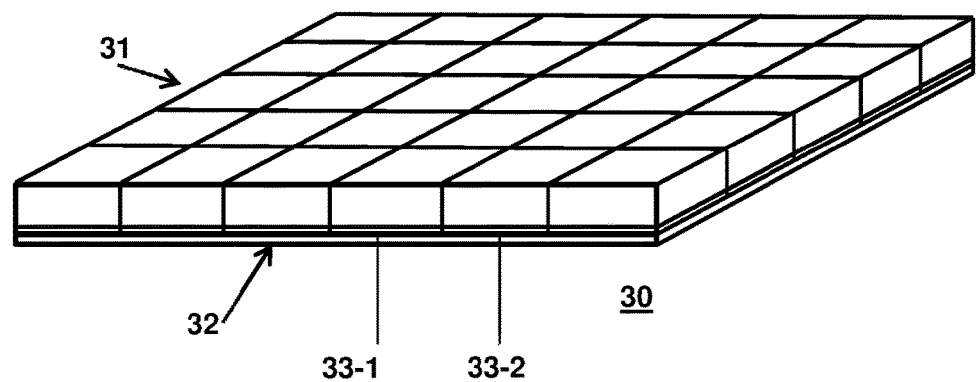
FIG. 1B depicts a schematic view of a photodetector substrate included in the device according to the embodiment in FIG. 1A
Figure 6A:
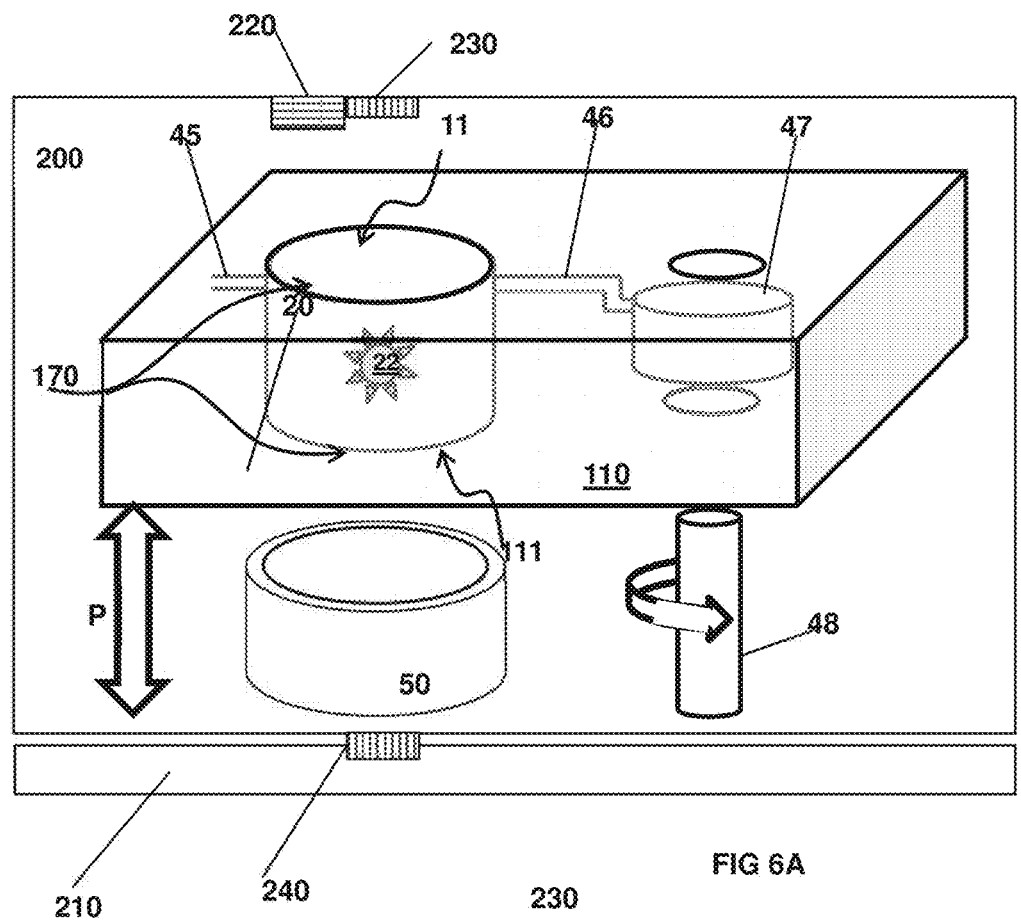
FIG. 6 shows another embodiment of a fluidics cassette geometry.
Figure 6B:
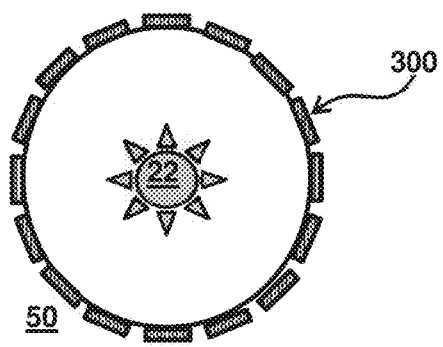

The detector wall part 12 is arranged so that the excitation spot 22 within the cassette projects emission radiation centrally relative to it in order to optimize light reception over a large area of a photodetector substrate 30 that is provided comprising an array 30 of photosensors further exemplified in FIG. 1B. The photodetector substrate 30 is conformal to at least the detector wall part 12 of the cassette 10. While many geometries are feasible, preferably the photodetector substrate 30 is planar, and the detector wall part is also planar for facilitating sliding insertion of the cassette in the placement provision. For optimizing light transmission, the cassette may be inserted while providing an optical transmission fluid between the detector substrate 30 and the cassette wall 12, which may further optimize removable placement of the cassette in the placement provision. In the embodiment of FIG. 6B, placement provision 210 is provided by suitable arrangement of photodetector substrates 30, but may be further provided with a sliding mechanism or locking mechanism not shown for removable placement of the cassette with its laser entry wall part 11 facing the laser transmission part, in particular, optic 6.

FIG. 1B provides a further schematic view of the photodetector 30 comprising an array of photosensors 31 formed in or on the substrate 32. For example a repeating patterned mosaic of bandpass filtered photosensors 31 is arranged in the array, e.g. a 2×2 pattern for Na, K and 2×Ca (for weaker Ca-signal); or a 3×3 pattern for 2×K, 4×Ca, Na-peak1, Na-dip and Na-peak2, etc. The number of sensors 31 may be provided in a spatially homogenous way over the array, wherein each sensor 31 is arranged with a bandpass filter 33-1, 33-2, etc. for detection of emission radiation of the plasma in a spectral part of interest. The ratio of sensors 31 with specific filters 33. for a spectral part of interest is provided by a ratio of amplitudes of a detection signal for emission lines of interest in the emission radiation of the plasma. In addition, smaller amplitude signals are preferably detected by sensors 31 with corresponding spectral filters 33 centred along the optical axis, in order to minimize losses.

A control mechanism (not shown) is arranged to impinge the laser beam on the excitation spot within the fluid analyte, in order to create the emission radiation; and detect the emission radiation of the plasma via the detector wall part by the array of photosensors 31 in the spectral parts of interest. In addition each photosensor 31 may comprise a notch filter for blocking the predetermined wavelength of the laser beam radiation 5. A preferred embodiment is applying a common notch filter 32 across all individual sensor elements 31 and their corresponding individual bandpass filters 33-1, 33.2, etc.

Figure 2:
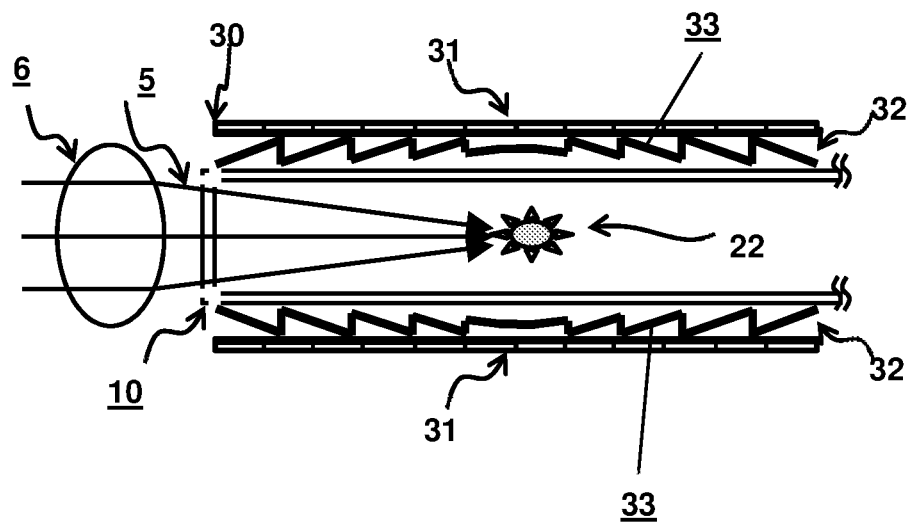
FIG. 2 depicts a further embodiment of the invention.

FIG. 2 shows an improvement of the embodiment in FIG. 1. In the depicted embodiment, a cassette 10 with a box geometry is formed of a disposable plastic. While the planar arrangement of the photodetector of FIG. 1 may already be effective in covering a large spatial angle (also called solids angle) of emission radiation emanent from the excitation spot 22, its collecting efficiency may be further enhanced by a Fresnel lens structure as shown in the FIG. 2, for directing the emission light toward normal incidence direction relative to the planar arrangement of the sensor substrate 32. In the embodiment, the Fresnel lens is provided in the substrate 32 of the photodetector 30. The Fresnel structure 33 can be provided by suitable milling of a glass or optical plastic substrate 32. Or by moulding of the plastic cassette wall.

Figure 3:
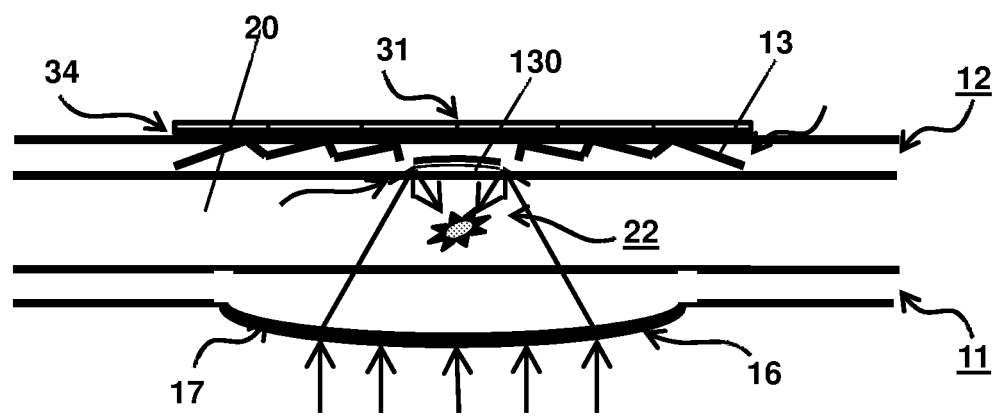
FIG. 3 shows another embodiment of the invention.

FIG. 3 shows an alternative to the FIG. 2 arrangement, wherein the detector wall 12 of the cassette may be provided with the Fresnel structure 13. The Fresnel structure is arranged to optimize the collecting efficiency of emission radiation at least in a spatial angle relative to the excitation spot larger than 0.5 pi steradians. This steradian angle value is preferably set to a value where the incidence angle of emission light exceeds a certain threshold associated with the detecting efficiency of the sensor 31, which may in practice be in the order of 0.5-1 pi steradians.

A further difference is found in the central focussing part of the Fresnel lens 13 i.e. in an area smaller than e.g 0.5 pi steradians, which is provided with a dichroic hot mirror coating acting as a focussing mirror 130 for incident laser radiation 5, that enters the cassette from below. For example, it may be provided by a laminate of molded lens geometries of different refractive indices in optical plastic material forming detector wall part 12. This arrangement has as advantage that the optical path through the dialysate is relatively short, since the laser radiation only travels the thickness of the cassette, instead of a length direction, preventing fluency losses and undesired heating of the analyte 20. An additional advantage is that the laser power density upon entry through the cassette wall can be significantly lower, because additional focussing is realized via reflection inside the analyte fluid (which doubles function as a coolant here). In addition or alternatively, the cassette may be provided with the laser entry wall part 11 comprising a laser beam focusing lens 16. To ensure that laser radiation does not enter the detector 30, a common notch coating 34 may be applied to the array of detectors 31.

In the embodiment of FIG. 3, absent the cassette in the placement provision, laser light cannot focus, enhancing robustness and security of the application. By providing the Fresnel structure in the detector wall part 12, grazing angle losses are prevented and all optical interfaces between fluid 22 and detector wall, and photodetector substrate 31 can be tuned in refractive indices of the optic interfaces. The focusing lens structure 16 may be further provided with a dichroic cold mirror coating 17, that is arranged to reflect emission radiation towards the detector wall part.

The embodiment in FIG. 3 has a laser entry wall that functions as a highly transmissive first focusing plano-convex lens 16 for the laser beam. This lens is, combined with a dichroic mirror layer 17 making it simultaneously highly reflecting for the light emitted by the plasma due its convex surface comprising a dichroic cold mirror. A practical example is using a Nd:YaG laser at 1064 nm for excitation, whilst the characteristic emissions to be detected are located at much smaller wavelengths e.g.:

Carbon (C) 247.88 nm
Magnesium (Mg) 279.60, 280.30, 285.30, 516.50, 518.40, 518.90 nm
Silicon (Si) 288.20 nm
Aluminum (Al) 308.30, 309.36, 394.50, 396.20 nm
Calcium (Ca) 315.90, 318.02, 393.40, 396.86, 422.60, 442.50, 443.50, 445.50, 458.12, 458.60, 457.80, 487.80, 558.90, 559.40, 559.90, 610.30, 612.30, 616.20, 643.90, 646.30 nm
Manganese (Mn) 323.60, 325.20 nm
Iron (Fe) 373.80, 527.00 nm
Titanium multiple peaks between 428 and 432 nm, 452.70, 496.40, 504.10, 526.30, 526.60 nm
Nitrogen (N) 460.70 nm
Potassium (K) 766.49, 769.90 nm
Sodium (Na) 588.90, 589.60, 651.30 nm Thus structure 16 functions as a first focusing lens for the laser and due to the dichroic cold mirror 17, simultaneously reflects and bundles emission radiation towards the detector wall part. The laser radiation then is further focussed to a discharge plasma by hot dichroic mirror 130, which, however is transparent for the wavelengths emitted by the plasma. This embodiment thus addresses the problem of lowering the laser beam energy density at the entry wall, while raising photon collection efficiency. The folded focusing path furthermore allows to keep the cassette thin, which is an advantage for miniaturization.

Figure 4:
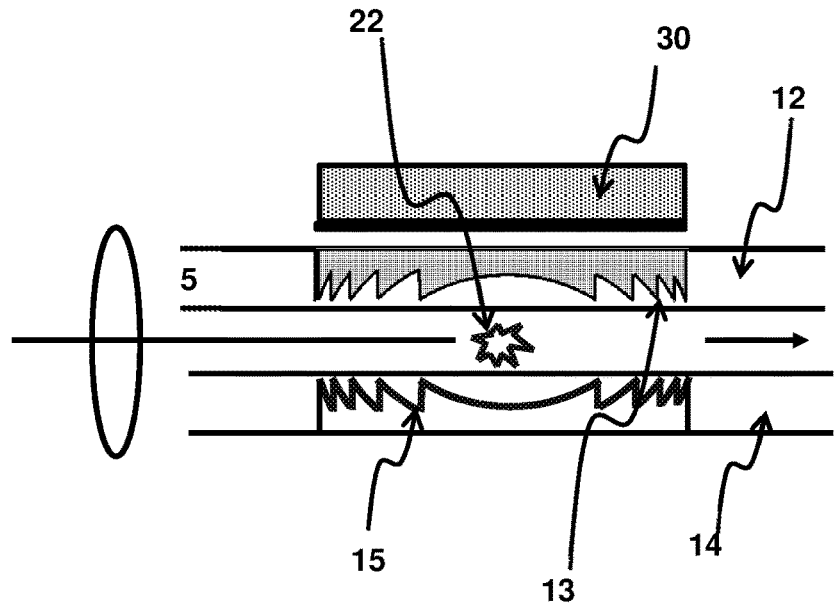
FIG. 4 shows yet another embodiment of the invention.

FIG. 4 shows a further embodiment that is arranged to reflect emission radiation to the detector wall part 12. To this end a Fresnel mirror structure 15 may be integrally formed in the cassette wall material of mirror wall part 14. In the present case the mirror wall part 14 is arranged opposite to the detector wall part 12, relative to the excitation spot, so that emission radiation of a spatial angle of more than 3 pi steradians is directed to the detector substrate. The Fresnel structure 15 may be a physical structure formed by moulding etc. and provided with an optically reflective coating, e.g. a metal coating on the mirror wall part 14. This coating may also be a cold mirror, thus reducing the amount of scattered laser light to reach the photodetector array.

Figure 5:
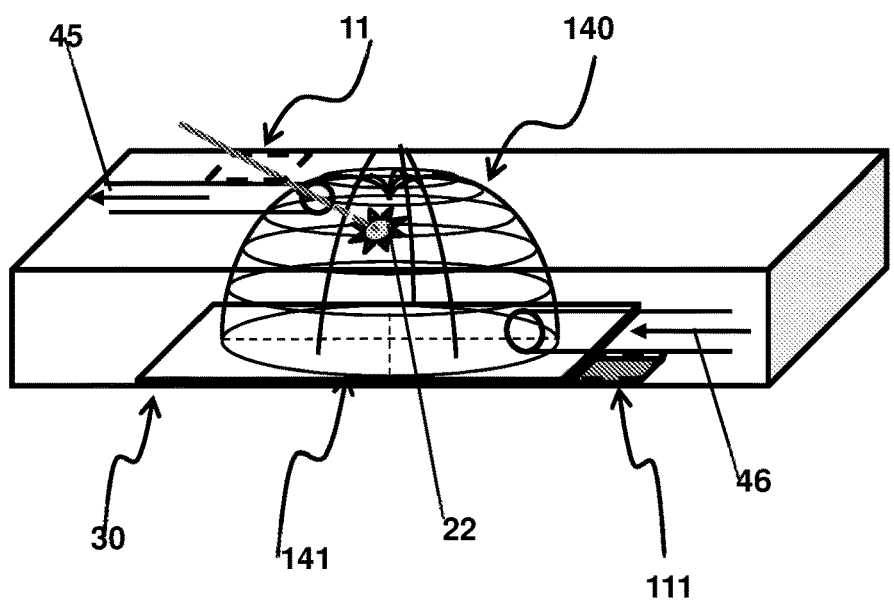
FIG. 5 shows a schematic setup of a fluidics cassette system for renal dialysis

FIG. 5 shows another embodiment of a cassette geometry having non-imaging collection optics. Only the cassette part is shown with the excitation spot 22. In the shown example, in a box geometry, a cassette suitable for holding a fluid analyte with entry ports 45 and exit ports 46 giving access to an optically designed holder space having a laser entry wall part 11, laser exit wall part 111 and a detector wall part 12. Laser exit wall part 111 may guide to a laser beam dump not shown. The holder space in a non imaging optic is a suitably shaped non-spherical optic such as a parabolic mirror piece 140 coated with e.g. a silver coating and e.g. having a bi-convex lens 141 arranged at its end. The non-imaging optic is, similar to the mirror suited to direct radiation emitted from excitation spot 22 towards the photodetector in a way similar to the mirror wall part 14 in FIG. 4.

Further Embodiments

In further embodiments, other geometries of the photodetector may be used formed by the array of photosensors provided on a substrate, e.g. in a cylindrical form. In the shown embodiment of FIG. 6A, a cassette 110 is shown e.g. as part of a renal dialysis machine, which can e.g. be used for haemodialisys (HD) or peritoneal dialysis (PD). In HD applications, patient's blood is lead through a dialysis filter, cleaned and fed back to the arterial circulation. The dialysis filter has e.g. a semipermeable membrane having on one side blood, and on the other side dialysate that cleans the blood. The dialysate may be used for a single pass and then be discarded, or it may be regenerated in a sorbent system for multipass.

Especially when regenerating the dialysate, it is important to monitor and maintain a proper balance of electrolytes in the dialysate, in particular, of Na+, K+ and Ca2+. Too high Ca2+ induces risks of atherosclerosis, and too low may result in osteoporosis. Excessive Na+ may increase blood pressure, where low levels will result in low blood pressure. Also K+ is a critical electrolyte for which abnormal levels may lead to heart rhythm problems (arrhythmia) or even heart failure. Also such electrolyte monitoring is of importance for single pass systems.

In PD dialysis, the peritoneal membrane in the abdominal cavity is used as dialysis filter, so that no extraneal membrane is used. Also for this application, the disclosed electrolyte sensor system may be applied both for single pass and multiple pass sorbent/regenerating systems.

Instead of being provided as part of the placement provision with e.g. a single sliding movement, the cassette 110 is now (after sliding in) additionally lowered over a matching photodetector 200, that contains an array of photosensors 50. FIG. 6B shows a top view of the cassette, showing an axial side of it. By the cylindric arrangement 300 of the array of photosensors, the excitation spot 22 is covered in all radial directions. In addition, a Fresnel structure (not shown) may be provided per photosensor along the axial direction to further optimize the collecting efficiency along the cassette cylinder. The cylindrical optical flow-through cuvette 111 (with inlet/outlets 45 & 46) is incorporated within cassette 110 and has transparent side walls. This cuvette part can be lowered into the mechanically matching photodetector array 50. The vertical movement is illustrated by arrow P. The cassette 110 has axial sides (top and bottom) that function as laser entry wall part 11 and laser exit wall part 111, respectively, opposite the laser entry wall part 11. These wall parts may be provided with a dichroic cold mirror coating 170, in order to reflect the plasma emission light back into the analyte towards the detector substrate 300. Laser entry wall parts 11 and laser exit wall part 111 may in practice be structurally identical. Laser exit wall part 111 may be provided, in use, adjacent to a beam dump structure 240 at the bottom of detector 50 that is provided in the placement provision, arranged for removeable placement (schematically depicted with arrow P) with its laser exit wall part adjacent the beam dump structure. This embodiment is advantageous because it is fully compatible with existing driving mechanisms for pumps and/or valves that are known within the art (e.g. illustrated by drive shaft 48 that can drive pump 47). In the shown embodiment for renal dialysis apparatus the spectral parts of interest are formed by characteristic optical emission lines of $Na^+$, $K^+$ and $Ca^{2+}$. FIG. 7 shows another advantageous embodiment, where the disclosed selective ion sensor principle is integrated into a dialysis filter module.

Figure 7A:
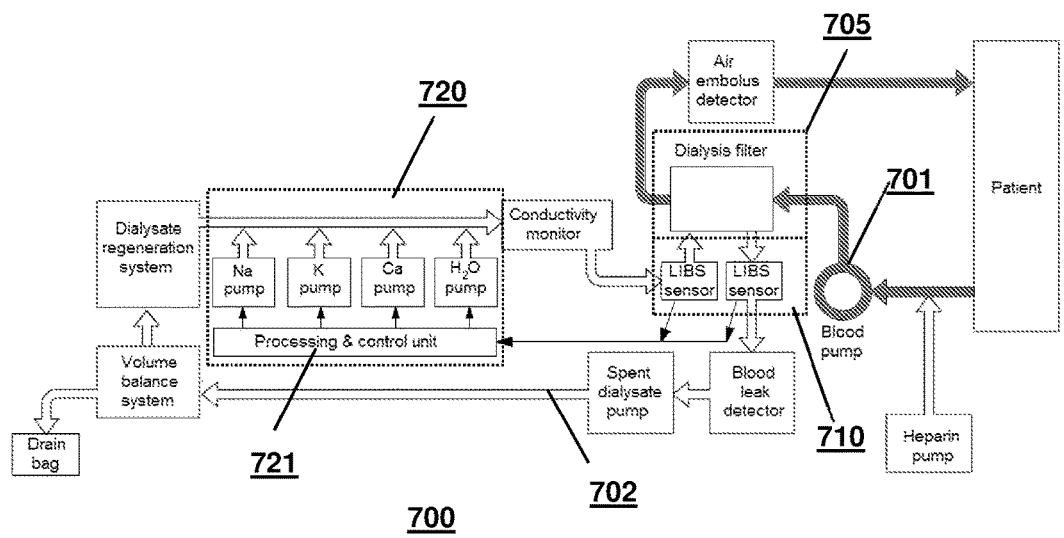
FIG. 7 shows another embodiment of a dialysis filter cassette.

FIG. 7A shows an embodiment of a dialysis system 700 with a photodetector cassette arrangement 710 for performing laser induced breakdown spectroscopy in plural locations in a blood dialysis system. In the system 700 a blood circuit 701 is formed by extracting blood from a patient and guiding it through a dialysis filter 705. Various conventional elements are provided such as a heparin pump and air embolus detector. As shown in further detail in FIG. 7B, the dialysis filter couples the blood circuit 701 via dialysis filter 705 to a dialysate circuit 702.

Figure 7B:
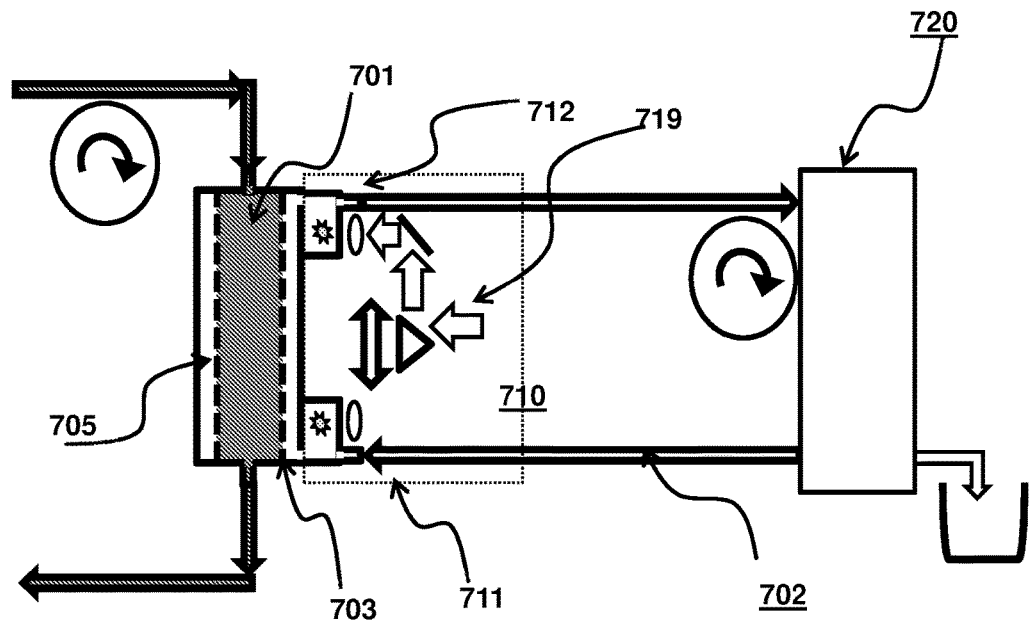

Advantageously, the dialysis filter 705 is provided with a detector cassette 710 having a photodetector 711 in the upstream part and a further photodetector 712 in the downstream part of the dialysate circuit 702 as further exemplified in FIG. 7B. The dialysate circuit 702 may be provided with a blood leak detector, dialysate pump and volume balance system (as known within the art). In an embodiment, a dialysate regeneration system, for instance, having a chemical sorbent, is provided. In such a system, electrolyte concentration levels of the dialysate circuit 702 can be critically monitored and maintained within specifications by a processing and control unit, in order to optimize the regenerated dialysate stream. In another embodiment (not shown), the dialysis circuit 702 has no regeneration system but for instance utilizes a conventional single pass provision with a preprepared dialysate volume. Advantageously, cassette 710 is connected to processing and control unit of an 721 electrolyte balancing system 720. For example, preprepared highly concentrated levels of Na+, K+, Ca2+ are available, which can be supplied in a controlled manner to individually replenish depleted ion levels. Adding water may be used to lower ion concentrations in the dialysate stream, all steered by a feed back loop controlled by controller 721. Accordingly, the photodetectors 711, 712 are connectable to blood filter 705 (also known as dialyzer filter) of a dialysis apparatus having a dialysate circuit, the dialysis apparatus comprising electrolyte balancing system 720, and controller 721, the controller 721 controlling electrolyte levels in the dialyte circuit by matching detected emission radiation in spectral parts of interest to a predetermined radiation level.

Also advantageously, in the dialysate circuit 702 detector cassette 710 may have upstream detector 711 that measures a difference in concentration levels for predetermined concentration levels, respective to a downstream detector 712. In this way, possible saturation in ion exchange of the chemical dialysate regeneration system may be detected. In FIG. 7B it is shown that the dialysate circuit 702 is in countercurrent with the flow of blood circuit 701, separated by a membrane 703, for example, a complex of hollow semi-permeable fibres, of course also all other membranes as known within the art can be applied. Assembly 710 (which also incorporates fluidic connectors) now can be snapped into the matching holder 705 with both photo detector arrays. For economic reasons the system may be equipped with an optical switching system 719 that facilitates using one excitation laser for two sensor locations 711, 712. For example a single laser may be directed to any of the sensor locations 711, 712, e.g. via a synchronous rotating polygon mirror, synchronous tuning fork mirror or a beamsplitter arrangement, etc. Accordingly the photodetector is connectable to blood filter 705 of a dialysis apparatus having a dialyte circuit, the photodetector 710 comprising first and second arrays 711, 712 respectively provided in an upstream and downstream part of the dialyte circuit 702, the method comprising monitoring the ion balance between dialysate and blood by comparing emission radiation respectively detected by the upstream and downstream arrays.

For an ion exchange mass balance the difference between the entry and exit concentration both must be known very precisely. Using the same laser for concentration measurements on entry and exit of the dialysis filter provides extra accuracy for ion mass balance registration. Slow drift in the laser power will namely have equal impact on both measurement locations for both concentration and flow measurement so that the drift falls out of the calculation for the difference.

While example embodiments were shown for systems and methods, also alternative ways may be envisaged by those skilled in the art having the benefit of the present disclosure for achieving a similar function and result. E.g. some components may be combined or split up into one or more alternative components. For example, the above-discussion is intended to be merely illustrative of the present system and should not be construed as limiting the appended claims to any particular embodiment or group of embodiments. Thus, while the present system has been described in particular detail with reference to specific exemplary embodiments thereof, it should also be appreciated that numerous modifications and alternative embodiments may be devised by those having ordinary skill in the art without departing from the scope of the present systems and methods as set forth in the claims that follow. The specification and drawings are accordingly to be regarded in an illustrative manner and are not intended to limit the scope of the appended claims In interpreting the appended claims, it should be understood that the word "comprising" does not exclude the presence of other elements or acts than those listed in a given claim; the word "a" or "an" preceding an element does not exclude the presence of a plurality of such elements; any reference signs in the claims do not limit their scope; several "means" may be represented by the same or different item(s) or implemented structure or function; any of the disclosed devices or portions thereof may be combined together or separated into further portions unless specifically stated otherwise. The mere fact that certain measures are recited in mutually different claims does not indicate that a combination of these measures cannot be used to advantage.

Where in the application use is made of terms as "hot" or "cold" mirrors, these terms are deemed known to the skilled in the art. Generally, these mirrors are formed by dichroic materials that are reflective to certain wavelengths and transmissive to certain other wavelengths. 'cold' and 'hot' mirrors here indicate dichroic mirrors. Where a 'cold' mirror is used, these materials reflect the relatively short wavelength emission radiation from the plasma discharge while transmitting the relatively long wavelength laser beam radiation, that is arranged to reflect emission radiation towards the detector wall part, which substantially raises the photon collecting efficiency of the photodetector, that may also be formed as other detector means, e.g. a photomultiplier tube, when the efficiency is brought to a sufficient detection level. Conversely, where a 'hot' mirror is used, these mirrors reflect the high intensity relatively long wavelength laser beam radiation, while transmitting the low intensity relatively short wavelength emission radiation. Depending on application, these hot and cold mirrors are geared to the transmitted laser radiation and selected parts of the electromagnetic spectrum of spectral parts of interest, i.e. associated with emission lines of chemical substances of interest.

The invention claimed is:

1. A spectroscopy device for inline monitoring of fluid analytes, the device comprising:
   a cassette suitable for holding a fluid analyte and having a laser entry wall part and a detector wall part, the laser entry wall part arranged to be optically transparent to laser radiation of a predetermined wavelength and the detector wall part arranged to be optically transparent for spectral parts of interest;
   a laser transmission optic for transmitting a laser beam of the predetermined wavelength from a laser system, via the laser transmission optic into the cassette, the laser transmission optic arranged to focus the laser beam through the laser entry wall in an excitation spot within the cassette in order to create a laser induced breakdown plasma within the fluid analyte, which emits optical radiation;
   a photodetector formed by an array of photosensors provided on a substrate, the photodetector substrate being conformal to at least the detector wall part of the cassette; each sensor in the array arranged with a bandpass filter for detection of emission radiation of the plasma in a spectral part of interest;
   a placement provision arranged for removable placement of the cassette with the laser entry wall part of the cassette facing the laser transmission part; and
   a control mechanism arranged to impinge the laser beam on the excitation spot within the fluid analyte, in order to create the laser induced plasma emission radiation and detect the emission radiation of the plasma via the detector wall part by the array of photosensors in the spectral parts of interest; wherein
   a notch filter is provided for blocking the predetermined wavelength of the laser beam radiation, wherein the detector wall part is arranged so that the excitation spot within the cassette projects emission radiation centrally relative to the array of photosensors; and wherein the laser entry wall part is provided with a dichroic cold mirror coating that is arranged to reflect emission radiation towards the detector wall part.

2. A device according to claim 1, wherein the photodetector substrate is formed in the placement provision, arranged for removable placement of the cassette with the detector wall part of the cassette adjacent the photodetector substrate.

3. A device according to claim 1, wherein the cassette is provided with the laser entry wall part comprising a laser beam focusing lens.

4. A device according to claim 1, wherein the cassette is provided with the detector wall part comprising a dichroic hot mirror arranged to focusing the laser beam to the excitation spot.

5. A device according to claim 1, wherein the cassette is provided with the detector wall part comprising a Fresnel lens structure arranged to optimize the collecting efficiency of emission radiation at least in a spatial angle relative to the excitation spot larger than 0.5 pi steradians.

6. A device according to claim 1, wherein the cassette comprises a mirror wall part, the mirror wall part arranged to reflect emission radiation to the detector wall part.

7. A device according to claim 1, wherein the cassette comprises a laser exit wall part opposite the laser entry wall part, and wherein a beam dump structure is provided in the placement provision, arranged for removeable placement with its laser exit wall part adjacent to the beam dump structure.

8. A device according to claim 7, wherein the laser exit wall part is provided with a dichroic cold mirror coating.

9. A device according to claim 1, wherein the photodetector substrate comprises an array of photosensors covering a spatial angle relative to the excitation spot larger than pi steradians.

10. A device according to claim 1, wherein the placement provision comprises a fluid inlet and a fluid outlet, the inlet and outlet in fluid communication with corresponding container fluid ports.

11. A device according to claim 1 integrated in a renal dialysis apparatus, wherein the spectral parts of interest are formed by characteristic optical emission lines of Na, K and Ca as well as Mg, Li, Al, Cu, Fe, C, O and P present within the laser induced breakdown plasma of the fluid analyte.

12. A device according to claim 1, wherein the photodetector substrate is planar and wherein the cassette has a box geometry and is formed of a disposable plastic.

13. A method of inline monitoring of fluid analytes, the method comprising:
providing a cassette suitable for holding a fluid analyte and having a laser entry wall part, the laser entry wall part arranged to be optically transparent to laser radiation of predetermined a wavelength and a detector wall part, arranged to be optically transparent for spectral parts of interest;
transmitting a laser beam of the predetermined wavelength from a laser system, via a laser transmission optic to the cassette, the laser transmission optic arranged to focussing the laser beam through the laser entry wall in an excitation spot within the cassette in order to create a laser induced plasma that emits optical radiation from within the fluid analyte, wherein the excitation spot within the cassette is central to the detector wall part the laser entry wall part provided with a dichroic cold mirror coating that is arranged to reflect emission radiation towards the detector wall part;
providing a photodetector formed by an array of photosensors provided on a substrate, the photodetector substrate being conformal to at least the detector wall part of the cassette; each sensor in the array arranged with a bandpass filter for detection of emission radiation of the plasma in a spectral part of interest;
removably placing the cassette with its laser entry wall part facing the laser transmission part;
impinging the laser beam on the spot within the fluid analyte, in order to create the plasma having the emission spectrum; and
detecting the emission radiation of the plasma by the array of photosensors in spectral parts of interest.

14. A method according to claim 13, wherein photodetector arrays are user connectable to a dialysis apparatus blood filter having a dialysate circuit with more than one optical cuvettes embedded in an upstream and downstream part of the dialysate circuit, the method comprising measuring selective ion balance by comparing emission radiation respectively detected by the upstream and downstream arrays.

15. A method according to claim 13, wherein the photodetector is connectable to a blood filter of a dialysis apparatus having a dialysate circuit, the dialysis apparatus comprising an electrolyte balancing system, and a controller, the controller controlling electrolyte levels in the dialysate circuit by matching detected emission radiation in spectral parts of interest to a predetermined radiation level.

* * * * *